United States Patent
Zagury et al.

(12)

(10) Patent No.: US 6,200,575 B1
(45) Date of Patent: Mar. 13, 2001

(54) NON-TOXIC IMMUNOGENS DERIVED FROM A RETROVIRAL REGULATORY PROTEIN ANTIBODIES PREPARATION PROCESS AND PHARMACEUTICAL COMPOSITIONS COMPRISING THEM

(75) Inventors: Jean-François Zagury, Paris; Bernard Bizzini, le Mesnil Saint Denis; Daniel Zagury, Paris, all of (FR)

(73) Assignee: Neovacs, Paris (FR)

( * ) Notice: Subject to any disclaimer, the term of this patent is extended or adjusted under 35 U.S.C. 154(b) by 0 days.

(21) Appl. No.: 09/570,915

(22) Filed: May 15, 2000

Related U.S. Application Data

(62) Division of application No. 08/913,221, filed as application No. PCT/FR96/00357 on Mar. 7, 1996.

(51) Int. Cl.⁷ .................................................. A61K 39/21
(52) U.S. Cl. .................... 424/208.1; 424/207.1; 514/2; 530/324; 530/350; 530/826
(58) Field of Search .............. 424/207.1, 208.1; 514/2; 530/324, 350, 826

(56) References Cited

FOREIGN PATENT DOCUMENTS

WO 89/12461    12/1989  (WO) .
WO 91/15224    10/1991  (WO) .
WO 91/18454    11/1991  (WO) .
WO 92/14755     9/1992  (WO) .
WO 93/22349    11/1993  (WO) .
WO 93/25235    12/1993  (WO) .
WO 94/15634     7/1994  (WO) .
WO 95/04546     2/1995  (WO) .

OTHER PUBLICATIONS

Brake et al., "Identification of an Arg–Gly–Asp (RGD) cell adhesion site in human innumodeficiency virus type 1 transactivation protein, tat" *Jour. Cell Biol.*, 111:1275–1282 (SE1990).

Brake et al., "Characterization of murine monoclonal antibodies to the tat protein from human immunodeficiency virus type 1", *Jour. Viro.*, 64:2:962–965 (FE1990).

Frankel et al., "cellular uptake of the tat protein from human immunodeficiency virus", *Cell*, 55:1189–1193 (1988).

Primary Examiner—Jeffrey Stucker
(74) Attorney, Agent, or Firm—Browdy and Neimark

(57) ABSTRACT

A non-toxic immunogenic compound, which may be administered to humans, is derived from an HIV-1, HIV-2, HTLV-1 or HTLV-2 viral regulatory protein by chemical processing using a coupling agent such as an aldehyde, or from a carrier protein activated by pre-processing using an aldehyde. This compound is capable of being recognized by antibodies to the viral regulatory protein and retains sufficient immunogenic properties to produce antibodies that neutralize or block the native protein, while losing at least 50% of the toxic biological properties of the native protein.

28 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear -continued

```
    (ii) MOLECULE TYPE: peptide (xi) SEQUENCE DESCRIPTION: SEQ ID NO:1:

His Gln Val Ser Leu Ser Lys Gln Pro Thr Ser Gln Pro Arg Gly Asp
1               5                  10                  15

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Glu Pro Val Asp Pro Arg Leu Glu Pro Trp Lys His Pro Gly
1               5                  10                  15
```

NON-TOXIC IMMUNOGENS DERIVED FROM A RETROVIRAL REGULATORY PROTEIN ANTIBODIES PREPARATION PROCESS AND PHARMACEUTICAL COMPOSITIONS COMPRISING THEM

This is a divisional of copending parent application Ser. No. 08/913,221, filed Sep. 8, 1997, which is a 371 of PCT/FR96/00357, filed Mar. 7, 1996.

The present invention relates to new retroviral immunogens which use retroviral regulatory proteins, the essential biological properties of which will have been inactivated beforehand such that their immunogenic properties are retained or increased, a process for their preparation and pharmaceutical compositions comprising them. These new "inactivated" immunogens can be used to induce active immunization in humans which is capable of preventing or correcting the deregulatory effects which the native proteins from which they are produced may help to produce.

The present invention also relates to new antibodies obtained by using these "inactivated" immunogens, processes for their preparation and pharmaceutical compositions for passive immunization which comprise them.

The Tat molecule is an HIV regulatory protein which is not found in the viral particle but is coded by the HIV-1 genome. Inside infected cells, this protein coded by the proviral DNA plays a transactivating role on viral or cell genes. However, this genetic regulatory protein can also be found outside cells in the circulating extracellular medium, excreted within the debris of dead cells in the native or fragmented state or by a secretion process. Its presence in the circulating medium explains the existence of anti-Tat antibodies detectable in some seropositive subjects. In this extracellular context of Tat, the terminal C segment which carries the RGD residues recognized by the integrins of the cell surface and the base region of the molecule (residues 45–70) enable it, as do bacterial toxins, to act on the non-infected cells of different tissues. The circulating Tat protein thus acts like a true viral toxin, can exert harmful effects on endothelial cells and, in combination with the growth factor BFGF, can contribute to the neoangiogenesis of Kaposi's sarcoma, which characterizes the AIDS disease. The circulating Tat protein can also aggravate the immunosuppression which becomes established progressively with AIDS, either by direct immunosuppressive action on the T cells or by helping to deregulate the production of interferon-α by the cells presenting the antigen, called APC (macrophages or dendrite cells).

Acquired immunodeficiency syndrome (AIDS) is defined clinically by opportunistic diseases due to immunosuppression or by Kaposi's sarcoma. Acquired immunosuppression, established progressively in the course of HIV infection, manifests itself biologically by the loss of immunological reactivity of T cells (cytostasis and the reduction in the production of IL2), after stimulation in the first instance by memory antigens, and then by alloantigens, and finally by mitogens (PHA). This immunosuppression is associated with excessive production of interferon-α and -γ.

The cytopathogenic mechanisms which induce immunosuppression are complex and involve various factors of viral origin, which act either directly on the immunity cells, T lymphocytes and APC, or indirectly via the cytokine system. The envelope protein gp120 which is carried by the HIV-1 particle and of which the extracellular presence is measured by the serum viral charge can thus induce anergy of T cells of phenotype CD4 directly. On their part, the HIV regulatory proteins, in particular Tat in its extracellular configuration of circulating viral toxin, also seem to induce a direct immunosuppression of T cells or other pathogenic effects, for example by the fact that in vitro T cells activated by a memory antigen or by anti-CD3 antibodies no longer proliferate in the presence of the Tat molecule. In addition, the circulating Tat protein seems to facilitate excessive production by the APC of interferon-α, a cytostatic and apoptogenic cytokine which is capable of amplifying the immunosuppresion and apoptosis observed with the AIDS disease. In fact, the secretion of interferon-α by macrophages no longer seems halted in the presence of Tat by a retroregulation (feedback), which in the normal state controls this production of interferon-α (refractory period).

Kaposi's sarcoma manifests itself clinically by the appearance of vascular nodules representing neoangiogenesis starting from endothelial cells. These cells, which have been activated by inflammatory processes generating the production of cytokines (interferon-γ, IL1 and IL6), produce BFGF (basic fibroblastic growth factor) and multiply. The proliferation of activated endothelial cells in vitro is increased by the presence in the medium of the Tat protein. The anti-Tat antibodies block the proliferative effects of the Tat protein in vitro. The action of Tat on the endothelial cells which carry adhesin from the family of integrins on their surface is explained by the presence of the RGD sequence recognized by these molecules.

The neoangiogenesis which underlies Kaposi's sarcoma in vivo was thus said to be promoted by the Tat regulatory protein in its extracellular configuration, which could be recognized, thanks to its terminal C fragment containing the RGD sequence, by the integrins of endothelial cells. Furthermore, the Tat may also act by its base region rich in residues K and R, and consequently be capable of bonding to heparin sulphate of the extracellular matrix, which concentrates the growth factor BFGF. The proliferation of endothelial cells induced by the growth factors is thus increased by the presence of Tat and generates neoangiogenesis. This effect on the growth of endothelial cells is reduced in vitro by the action of anti-Tat antibodies.

It thus appears desirable to block the harmful activity of retroviral regulatory proteins, in particular of Tat circulating in the extracellular media (blood, lymph, interstitial media . . . ), the true viral toxins.

As regards the HIV viruses, up to the present time attempts at vaccination have been made with the aid of structure proteins or fragments of structure proteins of these viruses, but never with the aid of regulatory proteins or fragments of regulatory proteins of these viruses.

Thus, it has been found, surprisingly, that like the bacterial toxins (tetanic, diphtheric or botulic), the toxic activity of which is neutralized by specific antibodies, the harmful effects of regulatory viral proteins, and in particular of Tat, a true toxin of HIV in its extracellular configuration—which these exert by immunosuppression of T cells, by deregulation of the production of interferon-α by the APC or by the neoangiogenesis which underlies Kaposi's sarcoma—are abolished in the presence of specific anti-Tat antibodies, as will be seen below in the experimental part.

The same applies to other regulatory proteins of viruses such as HIV-1, HIV-2, HTLV-1 or HTLV-2. It would thus be desirable to have available immunogens which can be administered to humans and are capable of producing such antibodies, and also to have available such antibodies, for both curative and preventive purposes. In fact, the compounds of the prior art used as immunogens may be toxic to humans (see, for example, WO-A-9118454), in particular those containing base regions. These are non-modified native fragments of Tat, Nef or Rev, in contrast to the present invention, which is based on the inactivation of these proteins or protein fragments.

The present Application thus relates to immunogenic compounds which can be administered to humans, since they are non-toxic, characterized in that they are derived from an HIV-1, HIV-2, HTLV-1 or HTLV-2 virus regulatory protein by chemical treatment with the aid of a coupling agent such as an aldehyde, or from a carrier protein activated by pretreatment with the aid of an aldehyde, preferably formaldehyde or glutaraldehyde, enabling them to be recognized by antibodies to the said regulatory protein, and to retain sufficient immunogenic properties to create antibodies which neutralize or block the said native protein, while having lost at least 50%, in particular at least 80%, more particularly 95%, of the toxic biological properties of the said native protein.

These compounds, by analogy to bacterial toxoids such as tetanus toxoid, will be qualified below as "toxoids".

In fact, like the conventional bacterial toxoids, they are devoid of proper toxicity, but are nevertheless capable of causing immunization by administration to a subject.

The chemical treatment below can be supplemented by a physical treatment, such as, for example, irradiation, and especially UV irradiation, with the aim of reducing the residual toxicity of the immunogenic compounds according to the invention.

The above toxoids can be prepared, for example, from a peptide which has a sequence identical or similar to a peptide sequence of a regulatory protein, such as Tat, and can be obtained, for example, by conventional peptide synthesis on resin or by genetic engineering. All these processes are well-known in the prior art.

In order to check that the modified regulatory protein or its modified fragment according to the invention is recognized readily by antibodies to the said native regulatory protein, the formation of antigen-antibody complexes, for example, can be checked immunologically by ELISA in the presence of specific antibodies, as will be seen below in the experimental part.

In order to determine whether the immunogenic properties of the regulatory protein have been retained sufficiently to create antibodies which neutralize the said native protein, mammals (rabbits, rats, mice) can be immunized, for example, with the aid of an immunogenic compound according to the invention and it can be checked that the antibodies produced neutralize the toxic activities of the regulatory protein, as will be seen for Tat in the experimental part.

In order to determine whether the modified regulatory protein has lost at least 50% of its toxic biological properties, it is possible to study, for example, the effect of the regulatory protein, such as inactivated Tat, on the immunosuppression of T cells or on the production of interferon-α by activated mononuclear cells of peripheral blood, or also on the neoangiogenesis induced by the regulatory protein.

The inactivation of the Tat regulatory protein is checked, for example, by "Tat rescue assay", using a Tat-deficient non-infectious HIV mutant cultured on the cell line HLM-1, replication of which depends on an exogenous supply of native Tat.

The immunogenic compound can be derived from any of the HIV-1, HIV-2, HTLV-1 or HTLV-2 virus regulatory proteins, and in particular Vif, Rev, Nef and Tat of the HIV-1 and HIV-2 viruses; Rev, Nef and Tat are used in particular, more particularly Rev and Tat, and preferably the latter.

The Tax protein of HTLV-1 or HTLV-2 may also be mentioned.

There may also be mentioned especially the regions outside the base regions of Tat and Rev, that is to say outside regions 49 to 57 of Tat and 35 to 50 of Rev, or overlapping these regions by at most 4 amino acids, preferably at most 2 amino acids, in particular the peptide HisGlnValSerLeuSerLysGlnProThrSerGlnProArgGlyAsp (SEQ ID NO:1).

"Derived from" or "to derive" an HIV1, HIV2, HTLV1 or HTLV2 virus regulatory protein is understood as meaning that the immunogenic compound can be made up of all or a fragment of the regulatory protein and may include one or more modifications in the amino acids of this protein or fragment, such as deletions, substitutions, additions or functionalizations, such as acylation of amino acids, to the extent that these modifications remain within the context specified above (absence of toxicity, immunological characteristics). For example, in general, the replacement of a leucine residue by an isoleucine residue does not modify such properties; the modifications should generally concern less than 30% of the amino acids, preferably less than 20%, and especially less than 10% over the homologous segments of the regulatory protein of at least 8 amino acids, in particular at least 12 amino acids. A fragment may comprise 8 to 60 amino acids, for example, preferably 12 to 40 amino acids and in particular 25 to 40 amino acids. Residues 65–80 in the C terminal of the Tat of HIV-1 may be mentioned by way of example.

Under preferential conditions, the immunogenic compounds of the invention comprise at least 50% of the total regulatory protein, preferably at least 70%, in particular at least 90%, and especially all or almost all the said protein.

Generally, as regards the modifications, homology or similarity between the modified immunogen and the native protein or part of native protein, as well as the dimensions of the immunogenic compound, and furthermore the methods of use or of coupling of the immunogenic compound according to the invention to an immunogenic protein, such as the tetanic toxoid, reference may be made in particular to WO-A-86/06 414 or to EP-A-0.220.273 or also to PCT/US.86/00831, which are equivalents, the disclosure of which is incorporated here by reference.

The immunogenic compounds according to the invention can be used as follows:

An immunogenic compound according to the present invention is administered to a patient, for example subcutaneously or intramuscularly, in an amount sufficient to be effective at the therapeutic level, in a subject having need of such a treatment. The dose administered can range, for example, from 100 to 1,000 μg subcutaneously, once a month for three months, and then periodically according to the level of serum antibodies induced, for example every 2–6 months.

A composition according to the invention can be administered by any conventional route customary in the field of vaccines, in particular subcutaneously, intramuscularly, intravenously or orally. The administration can take place in a single dose or be repeated once or several times after a certain interval of time.

The present Application thus also relates to a curative or preventive pharmaceutical composition, characterized in that it comprises an immunogenic compound as defined above as the active principle. The immunogenic compound can be formulated by itself or mixed with a pharmaceutically acceptable excipient, such as an adjuvant.

The invention also relates to medicaments, characterized in that they comprise immunogenic compounds as defined above, that is to say the above immunogenic compounds, for their use in a method for therapeutic treatment of the human or animal body, and to the use of such an immunogenic compound for the preparation of a curative or preventive medicament intended for treatment or prevention of the harmful effects of the above regulatory proteins, and in particular Tat. In fact, the compounds according to the invention have lost their toxic properties and can therefore be administered to humans, as will be seen below in the experimental part.

The administration of immunogenic compounds according to the invention corresponds to an active immunotherapy. It may also be of interest to carry out a passive immunotherapy, that is to say to provide a patient directly with the antibodies which he requires to neutralize the harmful effects of HIV-1, HIV-2, HTLV-1 or HTLV-2 virus regulatory proteins.

These anti-regulatory protein antibodies can be obtained conventionally and, by way of example, after immunization of a mammal, human or animal, with the aid of an immunogenic compound as defined above, by cloning human B lymphocytes transformed by the Epstein Barr virus and then collection of the required antibodies secreted by the said transformed B lymphocytes, or also by genetic recombination from a library of phages.

The present Application thus also relates to such processes for the preparation of anti-HIV-1, -HIV-2, -HTLV-1 or -HTLV-2 virus regulatory protein antibodies, and in particular anti-Tat toxoid antibodies, and in particular a process for the preparation of an above antibody, characterized in that a mammal is immunized with the aid of an immunogenic compound as defined above.

The present Application also relates to an anti-HIV-1, -HIV-2, -HTLV-1 or -HTLV-2 virus regulatory protein antibody, and in particular polyclonal or monoclonal antibodies obtained from human or mammalian subjects immunized by carrying out the processes described above.

These specific antibodies may originate:

1. either from the subject himself, induced by an active immunization (vaccination) with a biologically inactivated but immunogenic regulatory protein, in particular Tat. Such an immunogenic compound in the case of, for example, Tat is called Tat-toxoid, by analogy to bacterial toxoids, 2. or from a foreign allo- or xenogenic organism, administered to the subject by passive immunization (serotherapy). Allogenic antibodies (in humans) could be generated in volunteer non-infected subjects after active immunization (vaccination) with an immunogenic protein or its derivatives according to the invention, in particular Tat (Tat-toxoid or peptide fragments of Tat according to the invention). These passively administered antibodies, whether allogenic (human) or xenogenic (animal), could be complete monoclonal or polyclonal antibodies or fragments F(ab')2 or Fab of the antibody.

"Anti-regulatory protein antibody" is understood as meaning monoclonal or polyclonal antibodies or fragments F(ab')2 or Fab of these antibodies, or also anti-regulatory protein antibodies obtained by genetic construction from a library of phages.

The allogenic antibodies of human origin are:
either polyclonal—which can be obtained in volunteer seronegative subjects immunized with an immunogenic compound according to the invention, in particular Tat-toxoid or peptide fragments of Tat.
or monoclonal, from specific clones of B cells transformed by the EBV virus of these immunized individuals (EBV-specific B lines).

The xenogenic antibodies originate from animals hyperimmunized with an immunogenic compound according to the invention, in particular Tat or its derivatives (Tat-toxoid, detoxified peptide fragments of Tat according to the invention), and are
either polyclonal, originating from hyperimmunized animals,
or monoclonal, obtained after hybridization according to the Kohler and Milstein technique on splenic cells or adenocytes with a myelomatous line, type x63, in particular x63AG3. In this case, horse or rabbit antibodies are preferred.

The present Application also relates to a process for the preparation of anti-HIV-1, -HIV-2, -HTLV-1 or -HTLV-2 virus regulatory protein antibodies, characterized in that a mammal, human or animal, is immunized with an immunogenic compound as defined above.

The present invention also relates to a process for the preparation of monoclonal anti-HIV-1, -HIV-2, -HTLV-1 or -HTLV-2 virus regulatory protein antibodies, characterized in that B cells originating from individuals immunized by an immunogenic compound according to the present invention are used, the said B cells being transformed by the EBV virus and producing specific anti-HIV-1, -HIV-2, -HTLV-1 or -HTLV2 virus regulatory protein antibodies.

The above EBV+ cells can be cultured to produce the required antibodies. These cells, as has been seen, originate in particular from patients immunized with a native regulatory protein, or with an immunogenic compound according to the invention.

The present Application also relates to a process for the preparation of monoclonal antibodies according to the invention to an HIV-1, HIV-2, HTLV-1 or HTLV-2 virus regulatory protein, which is inactivated or non-inactivated, characterized in that hybridomas are prepared from mammals, in particular mice, from splenocytes or adenocytes, in particular mice immunized with a native regulatory protein or an immunogenic compound according to the invention, and myeloma cells, preferably of line x63, by processes well-known in the prior art (Kohler and Milstein).

The present Application also relates to a process for the production of anti-HIV-1, -HIV-2, -HTLV-1 or -HTLV-2 virus regulatory protein antibodies by the technology of genetic recombination, characterized in that an immunogenic compound as defined above is used as the immunogen.

The present Application also relates to fragments F(ab')2 or Fab of the said antibodies; these can be obtained by enzymatic digestion, for example.

The present invention furthermore relates to a process for passive immunization of subjects contaminated with the HIV virus using specific anti-HIV virus multiplication-regulating protein antibodies, and specifically anti-Tat antibodies, which neutralize or block the harmful effects of this protein in its extracellular configuration and are prepared as indicated above, or fragments F(ab')2 or F(ab) of these antibodies.

The present Application also relates to a process for active anti-HIV or -AIDS immunization using an immunogenic compound described above, combined with a constitutional (or structure) protein of an HIV virus, in particular the envelope glycoprotein gp 120 or gp 160 or a modified or non-modified peptide fragment thereof, or with an inactivated HIV virus, or with an HIV virus depleted in its genomic RNA, for example by alkaline hydrolysis.

The invention also relates to a process for active anti-HIV or -AIDS immunization using an immunogenic compound described above, combined with one or more immunogens based on inactivated cytokines, and in particular interferon- α, TGF-β or TNF. in fact, as will seen below in the experimental part, a combination of the effects of antibodies according to the invention to regulatory proteins, and anti-interferon-α antibodies in particular, completely restores the immunosuppression induced by HIV.

The present Application thus also relates to a composition comprising two immunogenic compounds, that is to say an immunogenic compound described above and an immunogenic compound which is capable of inducing antibodies to a cytokine, such as interferon-α or TNF-α, as described, for example, in WO-A-9118454, and to a composition comprising an antibody to a cytokine, in particular interferon-α, and an above antibody to a regulatory protein.

The present Application also relates to a process for active immunization, characterized in that an immunogenic compound as defined above, combined with a mineral, oily or synthetic immunity adjuvant, or also an immunogenic compound as defined above, coupled or combined with a protein which increases its immunogenicity, is used as the immunogen.

These immunizations can be realized both curatively and preventively.

A derivative of the Tat protein is. preferably used as the immunogen for all the processes above and below.

The present invention also relates to a process for hyperimmunization of HIV-1, HIV-2, HTLV-1 or HTLV-2 seronegative or seropositive subjects, characterized in that an immunogen as defined above is used for the production of hyperimmune human sera, which can be intended in particular for passive serotherapy by administration of purified specific antibodies or their fragments (F(ab')2 or Fab.

The invention also relates to a pharmaceutical composition comprising at least one anti-virus regulatory protein antibody as defined above or obtained by the above processes as the curative or preventive active principle.

The invention finally relates to an immunogenic compound or an above antibody for the preparation of a medicament intended for treatment of the harmful effects of an HIV-1, HIV-2, HTLV-1 or HTLV-2 virus regulatory protein.

In summary, and in particular, the present invention relates to the preventive or curative use on a seropositive subject or a subject suffering from ARC/AIDS of specific antibodies to block the harmful action of an HIV-1, HIV-2, HTLV-1 or HTLV-2 virus regulatory protein, and in particular circulating Tat. These specific antibodies may originate: 1. from the subject himself, induced by an active immunization (vaccination) with biologically inactivated but immunogenic Tat, called Tat-toxoid by analogy to bacterial toxoids, or 2. from a foreign allo- or xenogenic organism, administered to the subject by passive immunization (serotherapy). The allogenic antibodies (in humans) may be generated in volunteer non-infected subjects after active immunization (vaccination) with a regulatory protein, such as Tat or its derivatives (Tat-toxoid or peptide fragments of Tat according to the invention). These passively administered antibodies, whether allogenic (human) or xenogenic (animal), can be complete monoclonal or polyclonal antibodies or fragments F(ab')2 or Fab of antibodies.

Tat-toxoid, as has been indicated above, is understood as meaning a peptide or a Tat protein treated with a chemical agent. This treatment has caused the toxic biological properties of circulating Tat (immunosuppression of T cells; induction of the production of interferon-α by cells which produce interferon; neoangiogenesis of endothelial cells; blockage of the antiviral effect of interferon on the macrophages) to be lost to the molecule, but has retained the properties capable of inducing the formation of antibodies, when presented and prepared in an appropriate manner, coupled or not to a "carrier", aggregated or not, in the presence or absence of an adjuvant.

The concept of Tat-toxoid has been extended to immunogenic peptide fragments of Tat, that is to say a peptide sequence of Tat which is capable of inducing the formation of anti-Tat antibodies when presented in an appropriate manner, coupled or not to a carrier, in the presence or absence of an adjuvant.

The invention also relates to pharmaceutical compositions.

a) A pharmaceutical composition comprising a viral toxoid or a fragment or analogue of regulatory protein, in particular Tat, according to the invention as the preventive or curative agent.

b) A pharmaceutical composition comprising anti-Tat antibodies produced from organisms immunized against the said protein or its fragments F(ab')2 or Fab, according to the invention, as the preventive or curative agent.

The invention also proposes a kit comprising a vaccine pharmaceutical composition which, in addition to the active principle (Tat-toxoid or its derivatives or anti-Tat antibodies) can comprise an adjuvant and/or another immunogen having anti-retrovirus properties.

Finally, the invention proposes a pharmaceutical composition in a conventional galenical form. In particular, the active principle according to the invention is combined, in an amount sufficient to be effective from a therapeutic point of view, with a diluent or a carrier which is acceptable from a pharmaceutical point of view.

Experiment 1: Pathogenic Effects of Circulating Tat Protein

Immunosuppression of T cells in the presence of Tat:

The effect of Tat on activated T lymphocytes of peripheral blood has been investigated. Mononuclear cells (PMBC) and T lymphocytes (HLA 35 DR-) isolated by immunomagnetism were activated by anti-$CD_3$ antibodies in the presence or in the absence of the Tat molecule. After culture for 5 days, the cell proliferation was measured by incorporation of $H_3$-thymidine. The results showed that Tat inhibited the proliferation of HLA DR- T cells (85% inhibition at a concentration of 1.5 µg per ml). This inhibition disappeared in the presence of specific anti-Tat antibodies (Intracel, U.K.).

Experiment 2: Pathogenic Effects of Circulating Tat Protein

Inhibition of the effect of interferon on macrophages in the presence of Tat:

The effect of Tat on the antiviral action of interferon-α was measured by the conventional biological test using measurement of the cytopathogenic potency of the VSV virus on MDBK cells.

Effect of Tat on exogenous interferon

Increasing doses of Tat enabled the anti-viral potency of exogenous interferon to be inhibited from low concentrations according to a dose/effect curve for concentrations of Tat ranging from 1 to 20 µg/ml. In a representative experiment, the protective effect of interferon-α apparent up to the dilution 1/4,800 (corresponding to 150 I.U.) is reduced to the dilution 1/300 for concentrations of Tat of 10 µg/ml. At the concentration of 10 µg/ml of Tat, at the dilution of 4,800 of exogenous interferon the titre of VSV is thus increased from $10^{3.8}$ (interferon samples without Tat) to $10^{5.5}$ (interferon samples in the presence of Tat). In these experiments, the inhibition of the anti-viral effect of interferon-α by the Tat molecule is suppressed in the presence of specific anti-Tat antibodies (Intracel, U.K.), and also by the horse antibodies which we prepared (see examples below).

Experiment 3: Detection of the Tat Protein in its Extracellular Configuration in Subjects Infected by HIV-1.

Presence of anti-Tat antibodies in the serum of seropositive patients:

a) An ELISA study of serum anti-Tat antibodies using the native Tat molecule as the antigen was carried out on 50 seropositive subjects and 15 seronegative subjects. All the sera of the seronegative subjects and 20 sera of the seropositive subjects revealed no presence of anti-Tat antibodies with an optical density below the threshold (cut-off) (OD= 0.250). Among the 30 sera of subjects infected with HIV which exceeded the threshold, 6 have an OD greater than 0.500. No apparent correlation could be made between the presence of anti-Tat antibodies on the one hand, and the clinical condition and the number of CD4 cells per $mm^3$ of blood on the other hand.

b) An ELISA study of serum anti-Tat antibodies using various peptides of Tat as antigens was carried out on seropositive subjects at various stages of evolution of their HIV infection—asymptomatic subjects; patients showing pre-AIDS clinical symptoms (ARC) and patients suffering from AIDS. The results of this study are as follows:

1) The peptide sequences of Tat
MetGluProValAspProArgLeuGluProTrpLysHisProGly (SEQ ID NO:2). (residues 1–15 in the N terminal)
HisGlnValSerLeuSerLysGlnProThrSerGlnProArgGlyAsp (SEQ ID NO:1). (residues 65–80 in the C terminal) were recognized by the great majority of sera of seropositive subjects and by no serum of seronegative subjects (controls). The reactions were very positive, but no correlation could be demonstrated with respect to the evolution of the HIV infection and the number of CD4 in the subjects.

2) The other sequences studied were not recognized in an appreciable manner by the sera, whether from seropositive individuals or controls (see Table 1). Only a few rare sera for each sequence showed an optical density greater than the threshold (twice the mean of the control sera).

TABLE 1

| Peptide residues of Tat | Infected subjects* (72 sera) | | Control subjects (10 sera) | |
|---|---|---|---|---|
| | Positive sera** | Mean OD | Positive sera** | Mean OD |
| 1–15 | 67 | 0.43 | 0 | 0.08 |
| 9–20 | 0 | 0.26 | 0 | |
| 22–37 | 7 | 0.78 | 0 | 0.41 |
| 36–50 | 5 | 0.86 | 0 | 0.65 |
| 46–60 | 6 | 0.53 | 0 | 0.40 |
| 52–60 | 2 | 0.32 | 0 | 0.38 |
| 56–70 | 0 | 0.19 | 0 | 0.20 |
| 65–80 | 70 | 1.01 | 0 | 0.08 |

*The subjects infected by HIV are at various stages; asymptomatic subjects, patients suffering from ARC and patients suffering from AIDS.
**The reaction is considered positive (threshold) if the optical density is twice as high as the mean of the seronegative subjects.

3) It is interesting to note that the most reactive sequence (AA 65–80) is that containing the RGD residues recognized by the integrins.

EXAMPLE 1

Preparation of Immunogenic Tat Protein (Tat-toxoid)

Inactivation of the Tat protein in the presence of formaldehyde

Formaldehyde is added to a solution of Tat (1 mg/ml) in 70 mM disodium phosphate, pH 8.0, to the final concentration of 33 mM.

The mixture is incubated at 37° C. for 1, 3, 5, 7 and 9 days. At the end of each of the incubation periods, a sample is taken and the reaction with formaldehyde is blocked by addition of glycine to the final concentration of 100 mM.

Each sample is dialysed for 1 night at 4° C. against 100 times its volume of PBS (phosphate-buffered saline).

EXAMPLE 2

Preparation of Immunogenic Tat Protein (Tat-toxoid)

Inactivation of the Tat protein in the presence of glutaraldehyde

Glutaraldehyde is added to a solution of Tat (1 mg/ml) in 70 mM disodium phosphate, pH 8.2, to the final concentration of 0.026 M or 0.0026 M. The reaction with the glutaraldehyde is allowed to continue for various times varying from 1 min to 3 h. After the reaction time chosen, at the laboratory temperature, the reaction is blocked by addition of glycine to the final concentration of 100 mM. The various samples are dialysed for 16 hours at 40° C. against 100 times their volume of PBS.

EXAMPLE 3

Preparation of Immunogenic Tat Protein (Tat-toxoid)

Inactivation and simultaneous coupling to tetanic toxin of Tat

Glutaraldehyde is added to a mixture of tetanic toxin and Tat in a molar ratio of 1 to 15 in a 70 mM–100 mM phosphate buffer (pH varies from 6.8 to 8.2) to the final concentration (varying from 0.0026 M to 0.026 M), and the inactivation and coupling reaction is allowed to take place for various times (3–15 min) at the laboratory temperature. The reaction is blocked by addition of glycine to the final concentration of 100 mM and the various samples are dialysed for 16 hours at 4° C. against 100 times their volume of PBS.

EXAMPLE 4

Immunogenic Potency and Antigenicity of Tat-toxoids

Immunogenic Tat-toxoid in the mouse: Antibodies by ELISA

The immunogenic potency of various preparations of Tat which has been inactivated, either by formaldehyde (Tat-toxoid), or by glutaraldehyde (Tat-polan), or after coupling to tetanic toxin (conjugated Tat-tetanic toxin), that is to say the immunogenic compounds of examples 1 to 3, was determined in the mouse.

Swiss mice weighing 18–20 g were immunized by 2 subcutaneous injections of the immunogen of examples 1, 2 and 3 in the presence of Freund's complete adjuvant, the second being carried out 3 weeks after the 1st with 20 μg of preparation in emulsion in the presence of Freund's incomplete adjuvant.

15 days after the repeat injection, blood samples were taken intracardially. The anti-Tat antibodies in the sera were determined by ELISA. The optical density was measured at 490 nm.

The results obtained, summarized in Table 2, show that all the Tat preparations are immunogenic to various degrees, except for the conjugate Tat-TT treated with glutaraldehyde for a short time (3 minutes), which proved to be toxic and killed the mice within 24 hours (TT to weakly inactivated). It should be pointed out that the sera of the non-immunized mice respond below 0.200 (OD) to native Tat in the same way as to Tat-toxoid. Furthermore, these results show that the native Tat is recognized by the antibodies in the same way as the toxoid, which confirms their equivalent antigenicity and also justifies the use of the Tat-toxoid for immunization.

TABLE 2

| Preparations | Level of anti-native Tat antibodies optical density (OD) | Level of anti-Tat-toxoid antibodies (3 days) optical density (OD) |
|---|---|---|
| Tat-toxoid (1 day) | 0.320 | 0.331 |
| Tat-toxoid (3 days) | 0.465 | 0.494 |
| Tat-toxoid (5 days) | 0.998 | 0.901 |
| Tat-toxoid (9 days) | 0.807 | 0.780 |
| Tat-polan (1 min; 0.026M) | 0.718 | 0.706 |
| Tat-polan (15 min; 0.026M) | 1.564 | 1.452 |
| Tat-polan (60 min; 0.0026M) | 1.065 | 1.113 |
| Tat-polan (3 h; 0.0026M) | 0.194 | 0.210 |
| Conjugated Tat-TT (3 min; 0.0026M) | toxic | toxic |
| Conjugated Tat-TT (15 min; 0.0026M) | 1.987 | 1.897 |
| Conjugated Tat-TT (6 min; 0.026M) | 0.824 | 0.795 |
| Conjugated Tat-TT (15 min; 0.026M) | 1.642 | 1.556 |

EXAMPLE 5
Acute Toxicity

The toxicity of preparations of Tat-toxoid and Tat-polan was determined by subcutaneous injection to Swiss mice weighing 18–20 g. The preparations of Tat-toxoid (7 days) and Tat-polan (15 min; 0.026 M) were administered at a dose of 100 µg per mouse. The animals were observed for 7 days.

No manifest sign of toxicity was observed. The weight of the animals continued to increase. Macroscopic examination of the organs on autopsy revealed no anomalies.

EXAMPLE 6
Anti-Tat Antibodies

Anti-Tat antibodies were prepared as follows: The IgG fraction was isolated over a column of G protein from sera of mice immunized with Tat-polan. The fragments F(ab')2 were also prepared from the IgG fraction isolated by peptic digestion. The immunological reactivity of these fractions was checked by ELISA.

EXAMPLE 7
Biological Inactivity of Tat-toxoid

The various Tat-toxoids inactivated for 1, 3, 5 and 9 days from example 1 were tested in a test of the expression activity of the gene reporter chloramphenicol acetyl transferase (CAT) dependants of "long terminal repeat" (LTR) of HIV-1.

The principle of this test is as follows: Cells of the HeLa line containing the CAT gene under control of LTR of HIV are brought into contact with native Tat or the toxoids for 6 h. After culture for 24 h, the cells are lysed and the amount of CAT produced is measured by a test for the activity of CAT, which measures the percentage of acetyl-CoA attached to chloramphenicol. If the Tat molecule is active, there will be high percentage of acetylated chloramphenicol, and if not the percentage will be low. Culture of these adherent cells is carried out in a standard manner in RPMI, 10% FCS medium. The concentration of Tat added to give an effect/dose ranges from 1 µg to 10 µg per ml of supernatant.

The results shown here demonstrate that the Tat-toxoid is inactivated totally after 3 days, with a low residual activity at 1 day.

| Preparations | Acetylation of chloramphenicol (%) |
|---|---|
| Native Tat | 100 |
| Tat-toxoid (1 day) | 18 |
| Tat-toxoid (3 days) | 3 |
| Tat-toxoid (5 days) | 2 |
| Tat-toxoid (9 days) | 3 |

EXAMPLE 8
Absence of Pathogenic Effects of Tat-toxoid a) Absence of immunosuppression of T cells in the presence of Tat-toxoid (in contrast to experiments 1 and 2).

The effect of Tat-toxoid (5 days) on activated T lymphocytes of peripheral blood has been investigated. Mononuclear cells (PMBC) and T lymphocytes (HLA 35 DR-) isolated by immunomagnetism were activated by anti-$CD_3$ antibodies in the presence or absence of immunogenic compounds of example 1. After culture for 5 days, the cell proliferation was measured by incorporation of $H_3$-thymidine. The results showed that, in contrast to native Tat, the Tat-toxoid did not inhibit the proliferation of HLA DR- T cells. Thus, at a dose of 5 µg/ml in the culture in the presence of Tat-toxoid, the proliferation of cells was identical to that of the control.

b) Absence of inhibition of the effect of interferon-α on macrophages in the presence of Tat-toxoid:

The effect of Tat-toxoid on the antiviral action of interferon-α was measured by the conventional biological test using measurement of the cytopathogenic potency of the VSV virus on MDBK cells.

Effect of Tat-toxoid on exogenous interferon

In contrast to native Tat, equivalent doses of Tat-toxoid of example 1 did not enable the anti-viral potency of exogenous interferon to be inhibited. In a representative experiment, the protective effect of interferon-α apparent up to the dilution 1/4,800 (corresponding to 150 I.U.) is maintained in the presence of 50 µg of Tat-toxoid, while it is reduced to 1/300 with native Tat. At the dilution 4,800 of exogenous interferon, the titre of VSV is maintained at the level of the control at $10^{3.8}$ (interferon samples with Tat-toxoid), while it increases to $10^{5.5}$ (interferon samples in the presence of Tat).

EXAMPLE 9
Protective Role of Anti-Tat-toxoid Antibodies with Regard to the Effects of Native Tat.

Antibodies to Tat-toxoids of experiment 1 (treatment with formaldehyde for 3 days) were prepared in hyperimmunized horses. From these antibodies, fragments F(ab')2 were also prepared in accordance with the procedure described in example 6.

The antibodies, like the fragments F(ab')2, inhibit the various biological activities of native Tat in the various tests: Transactivation of the LTR of HIV (CAT test) (see example 7), immunosuppression (see experiment 1), inhibition of the effect of exogenous interferon-α on the culture (see experiment 2). Experiments 1 and 2 and example 7 were repeated with native Tat with or without preincubation of this native Tat for 1 h at 37° with the antibodies or fragments F(ab')2 at a dose of 40 µg of antibodies per 1 µg of native Tat. The results showed that the antibodies inhibit the action of native Tat.

EXAMPLE 10
Systematic Recovery of Cell Proliferation Due to the Combination of Anti-Tat Antibodies and Anti-interferon-α Antibodies: Synergism of Anti-Tat and Anti-interferon-α Antibodies.

It is found that PBLs (mononuclear cells of the peripheral blood) of healthy subjects infected in vitro with HIV-1 and cultured for 6 days had an immunosuppressive activity.

In fact, if such cells infected for 6 days (or non-infected) and irradiated are added in a proportion of 1 to 5 to autologous cells activated by the protein Staphylococcus enterotoxin B (SEB), it is found that after 4 days the proliferation of the autologous cells is reduced by 80% with respect to the controls (non-infected cells).

In this model, if anti-interferon-α antibodies are added to the culture of the cells infected in vitro, these cells then lose their suppressor effect in 50% of subjects. In 20% of the cases, suppressive cells lose 60% of their suppressor effect, and in 30% this suppressor effect is maintained significantly.

If anti-Tat antibodies (monoclonal, described in experiment 1, or polyclonal from the horse, of example 9) are added to anti-interferon-α antibodies, the cells infected in vitro lose their suppressor effect in 100% of the cases.

These experiments demonstrate the combined toxic role of Tat and interferon-α in the immunosuppression induced by HIV1, and that a combination of anti-interferon and anti-Tat antibodies restores a normal immunity.

EXAMPLE 11
Preparation of Immunogenic Nef Protein (Nef Toxoid)

Inactivation of the Nef protein in the presence of formaldehyde.

Formaldehyde is added to a solution of Nef protein (1 g/ml) in 70 mM disodium phosphate, pH 8.0, to the final concentration of 33 mM.

The mixture is incubated at 37° C. for 1, 3, 5, 7 and 9 days. At the end of each of the incubation periods, a sample is taken and the reaction with formaldehyde is blocked by addition of glycine to the final concentration of 100 mM.

Each sample is dialysed for 1 night at 4° C. against 100 times its volume of PBS (phosphate-buffered saline), and the Nef-toxoid is isolated.

EXAMPLE 12
Preparation of Immunogenic Nef Protein (Nef-polan)

Inactivation of the Nef protein in the presence of glutaraldehyde.

Glutaraldehyde is added to a solution of Nef (1 mg/ml) in 70 mM disodium phosphate, pH 8.2, to the final concentration of either 0.026 M or 0.0026 M. The reaction with the glutaraldehyde is allowed to continue for various times varying from 1 min to 3 h. After the reaction time chosen, at the laboratory temperature, the reaction is blocked by addition of glycine to the final concentration of 100 mM. The various samples are dialysed for 16 hours at 4° C. against 100 times their volume of PBS and the Nef-polan is isolated.

EXAMPLE 13

Immunogenic Potency and Antigenicity of Nef-toxoids

Immunogenic Nef-toxoid in the mouse: Antibodies by ELISA.

The immunogenic potency of various preparations of Nef which has been inactivated, either by formaldehyde (Nef-toxoid) or by glutaraldehyde (Nef-polan), that is to say the immunogenic compounds of examples 11 and 12, was determined in the mouse.

Swiss mice weighing 18–20 g were immunized by 2 subcutaneous injections of the immunogen of examples 12 and 13 in the presence of Freund's adjuvant, the second being carried out 3 weeks after the first with 20 μg of preparation in emulsion in the presence of Freund's incomplete adjuvant.

15 days after the repeat injection, blood samples were taken intracardially. The anti-Nef antibodies in the sera were determined by ELISA. The optical density was measured at 490 nm.

The results obtained, summarized in the table below, show that all the Nef preparations are immunogenic to various degrees. It should be pointed out that the sera of non-immunized mice give a level of response lower than 0.2 (in OD) in these ELISA tests.

These results show that the native Nef protein is recognized by the antibodies in the same way as the toxoid, which confirms their equivalent antigenicity and also justifies the use of the Nef-toxoid for immunization.

| Preparations | Level of anti-native Nef antibodies optical density (OD) | Level of anti-Nef-toxoid antibodies (3 days) optical density (OD) |
|---|---|---|
| Nef-toxoid (1 day) | 0.56 | 0.5 |
| Nef-toxoid (3 days) | 0.78 | 0.8 |
| Nef-toxoid (5 days) | 0.99 | 1.01 |
| Nef-toxoid (9 days) | 0.65 | 0.75 |
| Nef-polan (1 min; 0.026M) | 1.12 | 0.98 |
| Nef-polan (15 min; 0.026M) | 1.69 | 1.56 |
| Nef-polan (60 min; 0.0026M) | 1.31 | 1.41 |
| Nef-polan (3 h; 0.0026M) | 0.35 | 0.41 |

What is claimed is:

1. A method for reducing the titer of a circulating native HIV-1, HIV-2, HTLV-1 or HTLV-2 viral regulatory protein which is produced in a pathological viral condition, comprising causing a subject in need thereof to be immunized with a derivative of the native viral regulatory protein, which derivative is one which has lost at least 50% of a toxic biological property of the corresponding native viral regulatory protein and yet retains the capability of generating polyclonal antibodies cross-reactive with the corresponding said native viral regulatory protein.

2. A method in accordance with claim 1, wherein said loss of at least 50% of a toxic biological property is a loss of at least 50% of the property of immunosuppression of T cells, the property of deregulation is interferon-α production, the property of neoangiogensis, or the property of activation of CAT expression under the control of HIV-1 Long Terminal Repeat.

3. A method in accordance with claim 1, wherein said native viral regulatory protein is selected from the group consisting of the Nef, Tat, Vif and Rev regulatory protein of HIV-1 or HIV-2.

4. A method in accordance with claim 3, wherein said native viral regulatory protein is Tat.

5. A method in accordance with claim 4, wherein said loss of at least 50% of a toxic biological property is a loss of at least 50% of the property of immunosuppression of T cells, the property of deregulation of interferon-α production, the property of neoangiogenesis, or the property of activation of CAT expression under the control of HIV-1 Long Terminal Repeat.

6. A method in accordance with claim 1, wherein said derivative is the Tax regulatory protein of HTLV-1 or HTLV-2.

7. A method is accordance with claim 1, wherein said derivative has lost at least 80% of a toxic biological property of said native regulatory protein.

8. A method in accordance with claim 1, wherein said derivative has lost at least 95% of a toxic biological property of said native viral regulatory protein.

9. A method in accordance with claim 1, wherein said derivative having modifications is a full length native HIV-1, HIV-2, HTLV-1 or HTLV-2 viral regulatory protein having said modifications.

10. A method in accordance with claim 1, wherein said derivative comprises a fragment of the native viral regulatory protein.

11. A method in accordance with claim 10, wherein the native viral regulatory protein is Tat or Rev, and wherein said fragment is outside the basic region thereof or overlapping a basic region thereof by at most four amino acid residues.

12. A method in accordance with claim 1, wherein said derivative comprises all or a fragment of the native viral regulatory protein having modifications comprising deletions, substitutions or additions of the amino acid residues thereof, wherein less than 30% of the amino acids have been modified.

13. A method in accordance with claim 12, wherein less than 20% of the amino acids have been modified.

14. A method in accordance with claim 12, wherein less than 10% of the amino acids have been modified.

15. A method in accordance with claim 12, wherein said derivative having modifications is a fragment of a native HIV-1, HIV-2, HTLV-1 or HTLV-2 viral regulatory protein, which fragment has said modifications.

16. A method in accordance with claim 1, wherein said derivative comprises all or a fragment of the native viral regulatory protein having chemical functionalization of the amino acid residues thereof.

17. A method in accordance with claim 16, wherein said derivatives having chemical functionalization is a full length native HIV-1, HIV-2, HTLV-1 or HTLV-2 viral regulatory protein having said chemical functionalization.

18. A method in accordance with claim 16, wherein said derivative having chemical functionalization is a fragment of a native HIV-1, HIV-2, HTLV-1 or HTLV-2 viral regulatory protein, which fragment has said chemical functionalization.

19. A method in accordance with claim 18, wherein said derivative comprises said fragment having chemical functionalization of the amino acid residues thereof by treatment with an aldehyde.

20. A method in accordance with claim 19, wherein said fragment is selected from the group consisting of SEQ ID NO:1 and SEQ ID NO:2.

21. A method in accordance with claim 16, wherein the chemical functionalization is other than that which causes conjugation to a carrier protein.

22. A method in accordance with claim 16, wherein said chemical functionalization is by acylation or treatment with an aldehyde or with a coupling agent.

23. A method in accordance with claim 22, wherein said derivative comprises said native protein or fragment thereof having chemical functionalization of the amino acid residues thereof by treatment with a coupling agent so as to form an aggregate of the native protein.

24. A method in accordance with claim 23, wherein said coupling agent is glutaraldehyde.

25. A method in accordance with claim 22, wherein said derivative comprises said native protein or fragment thereof having chemical functionalization of the amino acid residues thereof by treatment with an aldehyde.

26. A method in accordance with claim 25, wherein said aldehyde is formaldehyde.

27. A method in accordance with claim 22, wherein said derivative comprises said native protein or fragment thereof having chemical functionalization of the amino acid residues thereof by acylation.

28. A method in accordance with claim 1, wherein said derivative comprises:
  (1) a fragment of the native viral regulatory protein;
  (2) all or a fragment of the native viral regulatory protein having modifications comprising deletions, substitutions or additions of the amino acid residues thereof, wherein less than 30% of the amino acids have been modified; or
  (3) all or a fragment of the native viral regulatory protein having chemical functionalization of the amino acid residues thereof.

* * * * *